United States Patent [19]

MacLeay et al.

[11] 4,009,157
[45] Feb. 22, 1977

[54] PRIMARY-ALIPHATIC α-HYDROXY AZOALKANES

[75] Inventors: Ronald Edward MacLeay, Williamsville; Chester Stephen Sheppard, Tonawanda, both of N.Y.

[73] Assignee: Pennwalt Corporation, Philadelphia, Pa.

[22] Filed: Mar. 21, 1974

[21] Appl. No.: 453,448

[52] U.S. Cl. .......................... 260/192; 260/2.5 R; 260/2.5 N; 260/566 B; 526/219; 526/242; 526/250; 526/265; 526/293; 526/319; 526/328; 526/335; 526/341; 526/344; 526/346

[51] Int. Cl.² .................. C07C 107/2; C08J 9/00; C08F 118/00; C08F 120/00

[58] Field of Search ..................... 260/192

[56] References Cited

UNITED STATES PATENTS

| | | | |
|---|---|---|---|
| 2,302,671 | 11/1942 | Buchman | 260/192 X |
| 2,778,818 | 1/1957 | Hyson et al. | 260/192 |
| 3,282,912 | 11/1966 | Benzing | 260/158 |
| 3,306,888 | 2/1967 | Mortimer | 260/192 X |
| 3,755,289 | 8/1973 | Nagaoka et al. | 260/192 |
| 3,775,395 | 11/1973 | Koyanagi et al. | 260/192 |
| 3,776,885 | 12/1973 | MacLeay | 260/158 |
| 3,812,095 | 5/1974 | Sheppard et al. | 260/192 |

OTHER PUBLICATIONS

Bracke et al., Index Chemicus, vol. 32, 108917 (1969).
Büttner et al. (I), Chem. Ber. vol. 104, pp. 1088–1103 (1971).
Büttner et al. (II), Chem. Ber. vol. 104, pp. 1104–1117 (1971).
Kempmann et al., Chem. Ber. vol. 101, pp. 3037–3046 (1968).

*Primary Examiner*—Floyd D. Higel
*Attorney, Agent, or Firm*—Barry A. Bisson

[57] ABSTRACT

Primary-aliphatic-α-hydroxyazo-alkanes having the structure:

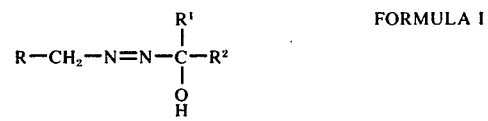

FORMULA I wherein R is hydrogen or a hydrocarbon radical containing 1 to 18 carbon atoms;
$R^1$ is the same as R except $R^1$ is not hydrogen;
$R^2$ is the same as R except $R^2$ is neither hydrogen, aryl, nor alkaryl;
$R^1$ and $R^2$ can together form an alkylene diradical;
R, $R^1$ and $R^2$ may be optionally substituted with the same or different groups.

The compounds of the invention are more stable than the corresponding tertiary aliphatic-alpha-hydroxyazoalkanes. The compounds of the invention are useful as foaming agents for polyester resins and initiators for free radical polymerization of vinyl monomers.

12 Claims, No Drawings

PRIMARY-ALIPHATIC α-HYDROXY AZOALKANES

BACKGROUND

This invention relates to primary-aliphatic (alkyl, cycloalkyl and aralkyl) azoalkanes containing one α-hydroxy substituent per azo group which are more thermally stable than corresponding tertiary azo compounds such as those disclosed in our Canadian Pat. No. 924,299 and therefore operate as vinyl polymerization initiators or curing agents for resins at higher temperatures. The new compounds hereof are also useful for preparing cellular structures from a variety of polymers as is more fully described in MacLeay et al. U.S. Application Ser. No. 453,446, now abandoned filed concurrently herewith.

So far as is known, none of the compounds hereof have been disclosed heretofore. Symmetrical α,α'-dihydroxyazoalkanes have been reported to form but are very unstable and essentially unisolatable [E. Schmitz, R. Ohme and E. Schramm, Ann. 702, 131 (1967)]. Consequently, they were not reported to be of any special value except as generators of diimide. Freeman and Rathjen, [J. Org. Chem. 37, 1686(1972)] reported the synthesis of 3-hydroxy-1-pyrazolines, cyclic examples of α-azocarbinols, by hydrolysis or hydrogenolysis of 3-acetoxy-1-pyrazolines. These carbinols are reported to undergo both acid and base-catalyzed ring opening to give ketones; no utility is reported for them.

t-Butyl-α-hydroxyalkyldiazenes have been prepared from t-butyldiazenes and aldehydes [S. Hunig and G. Büttner, Agnew. Chemie. Int. Ed. 8, 451(1969)], and from alkoxydiazenium salts and hydroxide ion [S. Hunig and G. Büttner, Chem. Ber. 104, 1088(1971)]. In the latter article Hunig and Buttner also prepared the following primary alkyl-α-hydroxyalkyldiazenes: 1-neopentylazo-1-hydroxymethane, 1-ethylazo-1-hydroxyethane, 1-methyl-azo-1-hydroxymethane, 1-ethylazo-1-hydroxymethane, and 1-methylazo-1-hydroxy-2,2-dimethylpropane. These prior art compounds do not foam the polyester resins nearly as efficiently as the hydroxy-azos hereof wherein the carbon attached to both the azo group and hydroxyl group is tertiary. In fact, as is developed more particularly herein, the azo compounds of this invention functioned effectively to foam polyesters where these prior art compounds failed entirely.

t-Alkyl-α-hydroxyazoalkanes [MacLeay et al. U.S. Application Ser. No. 149,041, filed June 1971], now abandoned and sec-alkyl-α-hydroxyazoalkanes [MacLeay et al. U.S. Application Ser. No. 453,447 filed concurrently herewith — ] are known. Their use in foaming resins is disclosed and claimed in MacLeay et al. U.S. Application Ser. No. 453,466. The primary-aliphatic-α-hydroxyazoalkanes hereof are very similar to the t-alkyl and sec-alkyl-α-hydroxyazoalkanes in their chemical properties except that the substitution of a primary-alkyl group for a t-alkyl or sec-alkyl group increases the thermal stability of the azo compound. In fact, the t-alkyl-α-hydroxyazoalkanes must be refrigerated to below 0° C. in order to maintain assay.

It is unobvious to prepare the novel I compounds based on the Prior Art. The methods used to prepare the known t-butyl-α-hydroxyalkyldiazenes do not apply. They were prepared from t-butyldiazenes and aldehydes [S. Hunig and G. Büttner, Agnew. Chemie Int. Ed. 8, 451(1969)] and from alkoxydiazenium salts and hydroxide ion [S. Hunig and G. Büttner, Chem. Ber. 104, 1088(1971)]. The alkoxydiazenium salts are derived from aldehydes.

In the latter article Hunig and Büttner also prepared some primary alkyl-α-hydroxyalkyldiazenes but again these compounds were derived from aldehydes. They did not and could not prepare alkyl-α-hydroxyldiazenes of this invention using the reactions they employed. Since Hunig et al. did not describe any use for their compounds, it was not obvious that the compounds of this invention would foam resins. In addition from the prior art there was no indication that the compound of this invention (derived from ketones) would be more efficient foaming agents than the α-hydroxyalkyldiazenes (derived from aldehydes) of the prior art.

MacLeay et al. U.S. application Ser. No. 149,041, supra, describes the synthesis of 2-t-butylazo-2-hydroxy-4-methylpentane by reacting 2-t-butylazo-2-chloro-4-methylpentane with sodium hydroxide. An attempt made to prepare the primary-alkyl-α-hydroxyazoalkanes by this method was unsuccessful in that the appropriate intermediate primary-alkyl-α-chloroazoalkanes could not be prepared by the method. Therefore a new method had to be devised. After intense investigation the reduction method described herein (and more particularly disclosed and claimed in MacLeay U.S. Application Ser. No. 453,451 now abandoned filed concurrently herewith, the contents of which are incorporated herein by reference) was developed.

The reduction of azohydroperoxides, where the azo and hydroperoxide groups are linked to the same carbon, was novel. It was found that the reduction had to be carried out on the basic side to prevent the acid decomposition of the azohydroperoxide.

BRIEF SUMMARY OF THE INVENTION

This invention relates to novel primary aliphatic-α-hydroxyazoalkanes having the formula:

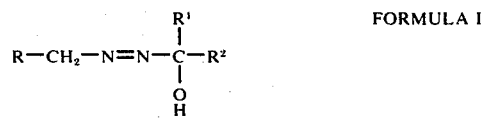

FORMULA I wherein
R is hydrogen or a hydrocarbon radical containing 1 to 18 carbon atoms, such as alkyl (normally 1 to 11 carbons, preferably 1 to 6); cycloalkyl, bicycloalkyl or tricycloalkyl (normally 3 to 12 carbons, preferably 5 to 8); aralkyl (normally 7 to 12 carbons, preferably 7 to 9); aryl (normally 6 to 14, preferably 6 to 10 carbons, particularly phenyl); alkaryl (normally 7 to 12 carbons, preferably 7 to 9);

$R^1$ is the same as R except $R^1$ is not hydrogen;

$R^2$ is the same as R except $R^2$ is neither hydrogen, aryl, nor alkaryl;

$R^1$ and $R^2$ can together form an alkylene diradical (normally 3 to 11 carbon atoms, preferably 4 to 7);

R, $R^1$ and $R^2$ may be optionally substituted with the same or different radicals such as lower alkoxy (1 to 6 carbon atoms), aryloxy (6 to 14 carbons, preferably phenoxy), cycloalkoxy (5 to 7 carbons), hydroxy, lower alkoxycarbonyl (2 to 5 carbons), aryloxycarbonyl (7 to 15 carbons), cycloalkylcarbonyloxy (6 to 8 carbons), cycloalkoxycarbonyl (6 to 8 carbons), alkanoyl (1 to 6 carbons), alkanoyloxy (1 to 6 carbons), aroyl (7 to 15 carbons), aroyloxy (7 to 15 carbons), alkenyl (2 to 6 carbons), cycloalkenyl (5 to 7 carbons), alkynyl (2 to 6 carbons), halogen (preferably chlorine or bromine), cyano or amino.

DETAILED DESCRIPTION OF INVENTION

The primary-aliphatic-$\alpha$-hydroxy azoalkanes (FORMULA I) are more thermally stable than their secondary- and tertiary-aliphatic counterparts and thus enable these compounds to normally operate efficiently as foaming agents without the stringent refrigeration requirements of the secondary and tertiary counterparts.

Compounds

The compounds of this invention are further illustrated hereinafter in lists of illustrative compounds, examples and methods of preparation.

Typical examples of R and $R^1$ are methyl, ethyl, propyl, i-propyl, butyl, i-butyl, sec-butyl, t-butyl, amyl, i-amyl, sec-amyl, t-amyl, neopentyl, hexyl, t-hexyl, n-octyl, t-octyl, n-nonyl, n-decyl, n-dodecyl, cyclopropyl, cyclobutyl, cyclopentyl, cyclohexyl, cyclooctyl, cyclododecyl, perhydronaphthyl, adamantyl, bicyclo[2.2.1]heptyl, benzyl, $\alpha$-cumyl, 2-($\beta$-naphthyl)ethyl, $\alpha$-methyl-$\alpha$-ethylbenzyl, $\alpha,\alpha$-diethylbenzyl, $\alpha$-ethyl-$\alpha$-propylbenzyl, 1-phenylcyclohexyl, 3,3,5-trimethylcyclohexyl, 4-t-butylcyclohexyl, methylcyclohexyl, trimethylcyclopentyl, 4-i-propylcyclohexyl, phenyl, o, m, and p-tolyl, naphthyl, triethylphenyl, phenanthryl, p-t-butylphenyl, m and p-methoxyphenyl, o, m, and p-bromo(or chloro)phenyl, xylyl, m-cyclopropylphenyl, p-cyclohexylphenyl, and p-i-propylphenyl. R may also be hydrogen.

Typical examples of $R^2$ are methyl, ethyl, propyl, i-propyl, butyl, i-butyl, sec-butyl, t-butyl, amyl, i-amyl, sec-amyl, t-amyl, neopentyl, hexyl, t-hexyl, 2-methoxy-2-methylpropyl, n-octyl, t-octyl, n-nonyl, n-decyl, n-dodecyl, cyclopropyl, cyclobutyl, cyclopentyl, cyclohexyl, cyclooctyl, cyclododecyl, perhydronaphthyl, adamantyl, bicyclo-[2.2.1]-heptyl, benzyl, $\alpha$-cumyl, 2-($\beta$-naphthyl)ethyl, $\alpha$-methyl-$\alpha$-ethylbenzyl, $\alpha,\alpha$-diethylbenzyl, $\alpha$-ethyl-$\alpha$-propylbenzyl, 1-phenylcyclohexyl, 3,3,5-trimethylcyclohexyl, 4-t-butylcyclohexyl, methylcyclohexyl, trimethylcyclopentyl, and 4-i-propylcyclohexyl.

Typical examples for $R^1$ and $R^2$ joined together are 1,1,3,3-tetramethyl-2-oxo-propylene, propylene, butylene, pentamethylene, hexamethylene, heptamethylene, octamethylene, undecamethylene, nonamethylene, 1,2, or 3-methylpentamethylene.

Typical examples of substituents borne by R, $R^1$ and $R^2$ are ethenyl, allyl, hexenyl, cyclopentenyl, methylcyclohexenyl, ethynyl, propynyl, hexynyl, methoxy, ethoxy, propoxy, hexoxy, isopentoxy, methylcyclopentoxy, cyclohexoxy, phenoxy, naphthoxy, chlorophenoxy, dimethylphenoxy, ethylphenoxy, cyclohexylphenoxy, acetoxy, propionoxy, isohexanoyloxy, cyclohexanecarbonyloxy, benzoyloxy, naphthoyloxy, chlorobenzoyloxy, methylbenzoyloxy, methylnaphthoyloxy, methoxycarbonyl, ethoxycarbonyl, butoxycarbonyl, cyclohexoxycarbonyl, phenoxycarbonyl, naphthoxycarbonyl, chlorophenoxycarbonyl, methylphenoxycarbonyl, methylbiphenyloxycarbonyl, acetyl, propionyl, valeroyl, cyclohexanecarbonyl, benzoyl, naphthoyl, chlorobenzoyl, methylbenzoyl, methylnaphthoyl, chlorine, bromine, iodine, fluorine, hydroxy, cyano.

Utility

The compounds of this invention (FORMULA I) evolve one mole of nitrogen gas when they are decomposed; in addition, other gases are evolved from the breakdown and/or disproportionation of the radicals formed. Thus they are useful in application where copious quantities of gases are desired such as in producing foamed polymers. In addition, many of the I compounds are relatively stable at room temperature but may be activated by a variety of acids to decompose quite rapidly at room temperature or below, generating gaseous products in the process. These compounds are useful in the preparation of rigid unsaturated polyester foams and other polymeric foams at ambient temperatures.

The compounds (I) are also useful as free radical generators, polymerization initiators, curing agents for unsaturated polyester resin compositions, and initiators for free radical initiated chemical reactions.

Polymerization

The I compounds are initiators for the polymerization or copolymerization of unsaturated monomers such as alkenes, dienes, perfluoroalkenes, vinyl halides, vinyl ethers, vinyl ketones, vinyl esters, vinylidene halides, alkenyl aromatics, allyl esters, allyl ethers and allyl ketones.

Illustrative polymerizable monomers include ethylene, propylene, styrene, chlorostyrene, vinyltoluene, vinylpyridine, vinyl pyrrolidone, vinylcarbazole, divinylbenzene, $\alpha$-methylstyrene, 1,3-butadiene, isoprene, chloroprene, vinyl acetate, vinyl propionate, vinyl laurate, vinyl benzoate, divinyl carbonate, allyl acetate, diallyl carbonate, allyl diglycol carbonate, allyl benzoate, diallyl phthalate, acrylonitrile and methacrylonitrile, acrylic acid, methacrylic acid and their esters and amides such as methyl, ethyl, n-butyl and 2-ethylhexyl acrylates and methacrylates and acrylamide and methacrylamide, maleic anhydride, maleic acid and fumaric acid and their esters, vinyl chloride, vinyl bromide, vinyl fluoride, vinylidene chloride, vinylidene fluoride, tetrafluoroethylene, hexafluoropropylene, and chlorotrifluoroethylene, methyl vinyl ether, n-butyl vinyl ether, allyl ethers, vinyl and allylketones, acrolein and mixtures thereof, especially ethylene, vinyl acetate, acrylonitrile, vinyl chloride, ethyl acrylate, methyl methacrylate and styrene.

Temperatures of from about 0° C. (e.g., with acrylonitrile) to about 260° C. (e.g., with ethylene), preferably about 20°–235° C., and initiator levels of about 0.005–1.0% or more (preferably 0.01–0.5%) by weight based on monomer, depending on azo half-life, temperature and monomer, are normally employed.

Curing

In curing unsaturated polyester resin compositions at suitable temperatures, compounds (I) are found to be effective curing catalysts.

Unsaturated polyester resins curable by the subject azos normally consist of an unsaturated polyester and polymerizable monomer.

The unsaturated polyester component is normally obtained by the esterification of one or more ethylenically unsaturated di- or polycarboxylic acids or their anhydrides, such as maleic acid, fumaric acid, glutaconic acid, itaconic acid, mesaconic acid, citraconic acid, allylmalonic acid, allylsuccinic acid, and others, with saturated or unsaturated polyalcohols, such as ethylene glycol, diethylene glycol, triethylene glycol, 1,2-propanediol, 1,3-propanediol, 1,2-butanediol, 1,4-butanediol, 2,2-dimethyl-2,3-propanediol, 2-buten-1,4-diol, 2-butyn-1,4-diol, glycerol, 2,2,4-trimethyl-1,3-pentanediol, 2,2,4,4-tetramethyl-1,3-cyclobutanediol, 1,4-di(hydroxymethyl)cyclohexane, 1,2,5-hexanetriol, pentaerythritol, mannitol and others. Mixtures of such acids and/or alcohols may also be used. The unsaturated di- or polycarboxylic acids may be replaced, at least partly, by saturated carboxylic acids such as adipic acid, succinic acid, secacic acid, hexahydrophthalic acid, and others, or by aromatic dicarboxylic acids, such as phthalic acid, iso- and terephthalic acids, and others and their anhydrides such as phthalic anhydride. The acids used as well as the alcohols employed may be substituted by halogen or other substituents, preferably by halogen. Examples of such suitable halogenated acids are, for instance, tetrachlorophthalic acid, 1,4,5,6,7,7-hexachloro-2,3-dicarboxybicyclo (2.2.1)-5-heptane and others, or their anhydrides.

The other component of the unsaturated polyester resin compositions is an ethylenically unsaturated monomer, preferably ethylenically unsaturated monomers such as styrene, chlorostyrene, vinyltoluene, methyl methacrylate, diallyl phthalate, dibutyl fumarate, acrylonitrile, triallyl cyanurate, α-methylstyrene, divinylbenzene, methyl acrylate, diallyl maleate, ethyl methacrylate, ethyl acrylate and others, which are copolymerizable with said unsaturated polyesters.

A preferred resin composition contains as the polyester component the esterification product of propylene glycol (a polyalcohol), maleic anhydride (an anhydride of an unsaturated dicarboxylic acid) and phthalic anhydride (an anhydride of an aromatic dicarboxylic acid) and as the monomer component styrene.

Initiating temperatures of about 20°–150° C. and azo levels of about 0.05 to 5.0% or more (preferably 0.1–2.0%) by weight of curable resin, depending on resin, azo half-life and temperature, are normally employed.

Foaming of Polyester Resins

The I compounds may be activated by acids to decompose at room temperature or below. This property can be used to effect foaming and gelling of unsaturated polyester resins. The α-hydroxyazo compound I are sensitive enough in most cases that the acidity of the polyester resin is sufficient to activate their decomposition. Gelling and foaming that ensues produces an exotherm, thereby effecting a cure (some of the I compounds having a high molecular weight require an activator to produce a low density foam). The cure of the polyester foam can be enhanced by the heat and/or the addition of a conventional curing agent such as a peroxide or an acid insensitive azo compound. The extent of foaming can be enhanced by the addition of an inert volatile compound that becomes gaseous during the early portion of the cure reaction. The bubble size can be decreased and the surface quality of the polymeric foam can be improved by the addition of anionic, cationic and non-ionic surfactants. The density of the polymeric foam can be decreased by the addition of materials such as hollow glass or ceramic spheres.

Polymerizable media suitable for foaming include polyester resins, polymeric molecules (containing two or three copolymerizable vinyl unsaturation only in the terminal or pendant positions) dissolved in suitable copolymerizable vinyl monomers, viscous syrups or polymers dissolved in monomers, epoxy-containing monomers, and the like. Use of some of the compounds (I) to prepare foamed polyester resins of varying densities is illustrated in the examples. A more complete description of the foaming utility is contained in copending application Ser. No. 453,446, of Ronald E. MacLeay et al for "Process For Preparing Foamed Structures".

Preparation of Novel Compounds

The novel I compounds of this invention are derived from primary-alkylhydrazines and primary-alkylhydrazones. There are numerous methods described in the literature for preparing primary-alkylhydrazines. The first method used herein was the method described by Rutter ["A Study of Some Reactions of the Monoalkylhydrazines", Univ. Microfilms 68–325(1967)] for the synthesis of n-octylhydrazine and n-dodecylhydrazine. The method involved the reaction of an excess of hydrazine with the corresponding bromide and separation of the primary-alkyl hydrazine by distillation (1).

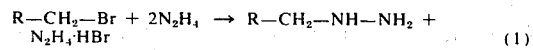

The second method employed herein was to react benzhydrazide with an aldehyde to form the desired benzoylhydrazone (2). The benzoylhydrazone was then hydrogenated over platinum oxide in ethanol to form the 1-benzoyl-2-primary-alkylhydrazine (3). The benzoyl group was hydrolyzed off with concentrated HCl (4). The resulting primary-alkylhydrazine hydrochloride was converted to the primary-alkylhydrazine by neutralizing with dilute NaOH (5). This method is essentially a combination of the methods described by Fox and Gibas (reduction step) [J. Org. Chem. 18, 994(1953)] and Ramsperger (hydrolysis step) [J. Am. Chem. Soc. 51, 918(1929)].

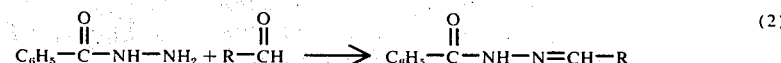

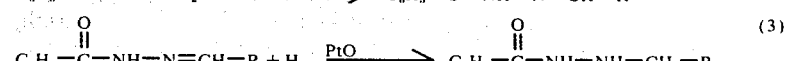

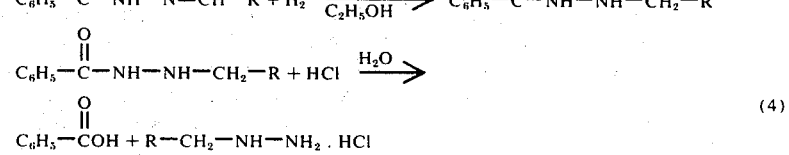

$$R-CH_2-NH-NH_2 \cdot HCl + NaOH \longrightarrow R-CH_2-NH-NH_2 \quad (5)$$

The primary-alkylhydrazones were prepared by refluxing a solution of the primary-alkylhydrazine with an equivalent amount of the desired ketone

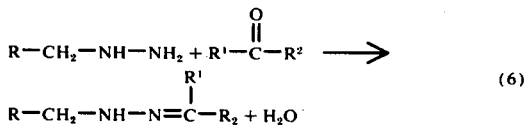

(6)

$$R-CH_2-NH-N=C-R_2 + H_2O$$

In the case of the less reactive ketones, the reaction can be carried out by azeotroping off the water from a benzene solution of the primary-alkylhydrazine and the desired ketone. Suitable ketones include the following non-limiting list of ketones: acetone, methyl ethyl ketone, methyl propyl ketone, methyl isopropyl ketone, methyl isobutyl ketone, methyl butyl ketone, 4,4-dimethylpentanone-2,2-octanone, cyclopentanone, cyclohexanone, cyclooctanone, cyclododecanone, undecanone-2, methyl cyclopropyl ketone, methyl cyclohexyl ketone, 4-t-butylcyclohexanone, 3,3,5-trimethylcyclohexanone, 2-methylcyclohexanone, acetophenone, diisobutyl ketone, diethyl ketone, 1,3-diphenylacetone, 1'-acetonaphthone, 2'-acetonaphthone, indanone, β-tetralone, propiophenone, pinacolone, benzylacetone, cyclohexylacetone, di-n-hexyl ketone, 3,5-dimethyl-4-heptanone, 2,4-dimethyl-3-hexanone, 5-methyl-2-hexanone, 10-nonadecanone, 4-octanone, 6-undecanone, 9-acetylanthracene, p-bromobutyrophenone, p-chloropropiophenone, 3,4-dimethylacetophenone, p-fluoropropiophenone, 8-ketotricyclo-[5.2.1.0$^{2,6}$] decane, 5-methoxy-2-tetralone, 1-adamantyl methyl ketone, cyclobutyl phenyl ketone, cyclopropyl phenyl ketone, cyclohexyl phenyl ketone, cyclopentyl phenyl ketone, 4-methoxy-4-methylpentanone-2, tetramethyl-1,3-cyclobutanedione, esters of levulinic acid such as allyl levulinate and n-butyl levulinate, acetonyl acetone, and 3-acetyl-1-propanol, all of which are commercially available.

The primary-alkyl-α-hydroxyazoalkanes were prepared by oxidizing the corresponding primary-alkylhydrazone to the α-hydroperoxyazoalkane with oxygen (7) and then reducing the hydroperoxide to the alcohol with a mild non-acidic reducing agent such as aqueous sodium sulfite (8).

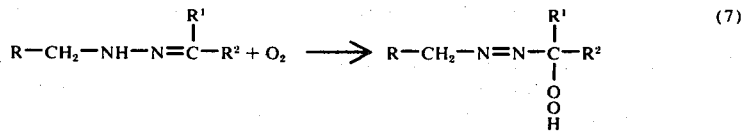

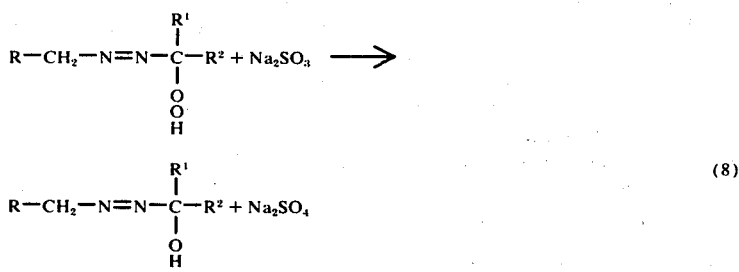

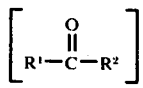

The α-hydroperoxyazoalkanes are prepared by bubbling oxygen into a solution of the corresponding primary-aliphatic hydrazone in an inert solvent until the hydrazone has been completely oxidized to the α-hydroperoxyazoalkane. The method is described in Application Ser. No. 88,248 now abandoned of R. E. MacLeay and O. L. Mageli and Application Ser. No. 88,249 now abandoned of R. E. MacLeay and C. S. Sheppard both filed Nov. 9, 1970. Most of the α-hydroperoxyazoalkanes are thermally unstable and shock sensitive so extreme care should be exercized in handling them. If it is desirable to isolate the final α-hydroxyazo, it is preferable to use a low boiling hydrocarbon, such as pentane or hexane, as a solvent.

Since both the α-hydroperoxyazoalkanes and the α-hydroxyazoalkanes are sensitive to acidic reagents, it is essential that the reducing system used be essentially neutral or basic. Dilute aqueous solutions of sodium sufite reduce the α-hydroperoxyazoalkane smoothly. On the other hand, dilute aqueous solutions of sodium bisulfite, which is somewhat acidic, give much lower yields due to acidic decomposition of the α-hydroperoxyazoalkanes. Due to the thermal instability of the α-hydroperoxyazoalkanes the reductions are usually carried out below 25° C. This requires cooling and slow addition of the reducing agent to control the exotherm generated in the reduction. Vapor phase chromatography offers a convenient method for monitoring the reduction.

The temperature range for the reductions should take into consideration the thermal stability of the starting azohydroperoxide and the final product. Therefore the reduction should be run below 50° C, preferably below 35° C, and most preferably below 25° C. Since the azohydroperoxide reacts very readily, the lower temperature limit will be controlled by the freezing point of the aqueous solution. Preferably it should be run above −10° C and most preferably above −5° C. Since the azohydroperoxide and the α-hydroxyazos are quite soluble in hydrocarbons, chlorinated hydrocarbons, alcohols, ethers, esters and nitriles, any of these inert solvents are suitable providing the reaction is not run below the freezing point of the solvent. Examples of such suitable solvents are pentane, hexane, heptane, octane, methanol, ethanol, isopropanol, propanol, n-butyl alcohol, isobutyl alcohol, t-butyl alcohol, nonane, decane, dodecane, cyclohexane, methylcyclohexane, cyclopentane, benzene (above 5° C), toluene, dichlorobenzene, trichlorobenzene, t-butylbenzene, xylene, methylene chloride, chloroform, carbon tetrachloride, perchloroethylene, mineral spirits, styrene, α-methylstyrene, diethyl ether, dipropyl ether, di-n-butyl ether, dioxane, tetrahydrofuran, ethyl acetate, methyl acetate, ethyl benzoate, acetonitrile and propionitrile. However, if the α-hydroxyazo is to be isolated, it is preferable to use the more volatile solvents. The concentration of the azohydroperoxide in the solvent can vary from 1% to 99% but for practical reasons it is preferable to use a concentration above 25%. For safety reasons it is preferable to use a concentration of 75% or less.

Due to the acid sensitivity of the α-hydroxyazo products and the azohydroperoxide starting material, it is essential that the pH of the reducing system be at pH 7 or above at the beginning and throughout the reduction. Aqueous sodium sulfite solution is the most preferred reducing system. The concentration of the solution can vary from ½% to a saturated solution. However, the more concentrated the solution, the slower it must be added to control the reaction exotherm. Another suitable reducing system would be hydrogen in the presence of hydrogenation catalysts such as Raney nickel, platinum on carbon, platinum oxide, palladium on charcoal, etc. It would be preferable to run these hydrogenations in the presence of a weak base to prevent acid decomposition of the azo-hydroperoxide or α-hydroxyazo.

Surprisingly we have found that this novel method of preparing α-hydroxyazoalkanes also applies to the compounds of the prior art, i.e., I compounds where $R^1$ would be hydrogen. We used this method to prepare four primary-alkyl-α-hydroxyazoalkanes of the prior art type (see Table IV) for comparison of foaming efficiencies in polyester resins with the novel I compounds.

The following are examples of novel compounds which fall within the scope of the I azo compounds:

1. 1-methylazo-1-hydroxy-1-cyclooctylethane
2. 1-ethylazo-1-hydroxy-1-cyclopropylethane
3. 1-propylazo-1-hydroxy-1-cyclohexylethane
4. 1-isobutylazo-1-hydroxy-1-cyclododecylethane
5. 1-butylazo-1-hydroxy-1-cyclopentylethane
6. 1-amylazo-1-hydroxy-1-(norborn-2-yl)ethane
7. 1-isoamylazo-1-hydroxy-1-(adamant-2-yl)ethane
8. 2-(2-methylbutylazo)-2-hydroxy-1-phenylpropane
9. 2-neopentylazo-2-hydroxy-4-(β-naphthyl)butane
10. 2-hexylazo-2-hydroxy-1-(p-t-butylphenyl)propane
11. 1-heptylazo-1-hydroxy-1-phenylethane
12. 2-octylazo-2-hydroxy-5-phenylpentane
13. 1-nonylazo-1-hydroxy-1-(phenanthr-2-yl)ethane
14. 1-decylazo-1-hydroxy-1-(naphth-2-yl)ethane
15. 1-undecylazo-1-hydroxycyclododecane
16. 1-dodecylazo-1-hydroxycyclobutane
17. 1-cyclohexylcarbinylazo-1-hydroxycyclooctane
18. 1-cyclopropylcarbinylazo-1-hydroxycyclodecane
19. 2-cyclododecylcarbinylazo-2-hydroxynorbornane
20. 2-cyclopentylcarbinylazo-2-hydroxy(2.2.2-bicyclooctane)
21. 2-(norborn-2-ylcarbinylazo)-2-hydroxyadamantane
22. 2-(2.2.2-bicyclooct-2-ylcarbinylazo)-2-hydroxy-4-methylpentane
23. 2-(adamant-1-ylcarbinylazo)-2-hydroxy-4-phenoxy-4-methyl-pentane
24. 2-(2-phenylethylazo)-2,4-dihydroxy-4-methylpentane
25. 2-[3-(β-naphthyl)propylazo]-2,5-dihydroxypentane
26. phenyl 4-[β-(3,4-dimethylphenyl)ethylazo]-4-hydroxyhexanoate
27. 1-benzylazo-1-hydroxy-1-(p-chlorophenyl)ethane
28. 1-(phenanthr-1-ylcarbinylazo)-1-hydroxy-1-(m-bromophenyl)ethane
29. 1-(β-naphthylcarbinylazo)-1-hydroxy-1-(p-fluorophenyl)ethane
30. 1-(p-chlorobenzylazo)-1-hydroxy-1-(p-iodophenyl)ethane
31. 2-(m-bromobenzylazo)-2-hydroxy-4-(benzoyloxy)butane
32. 1-(p-fluorobenzylazo)-1-hydroxy-1-(p-cyanophenyl)ethane
33. 2-(m-methoxybenzylazo)-2-hydroxy-5-aminopentane
34. 2-(β-methoxyethylazo)-2-hydroxytetrahydronaphthalene
35. 4-(β-cyanoethylazo)-4-hydroxy-2,6-dimethylheptane
36. 2-(β-phenoxyethylazo)-2-hydroxydecane
37. 2-[β-(ethoxycarbonyl)ethylazo]-2-hydroxyindane
38. 1-(β-carboxyethylazo)-1-hydroxy-1-(anthracen-9-yl)ethane
39. 3-[β-(phenoxycarbonyl)ethylazo]-3-hydroxyheptane
40. 2[β-(benzoyloxy)ethylazo]-2-hydroxy-3,3-dimethylbutane
41. 1-(β-aminoethylazo)-1-hydroxy-1-phenylpropane

EXPERIMENTAL

A. 1. General Procedure A for the Preparation of Primary-alkylhydrazones

Into a 250 ml 4 neck flask equipped with a magnetic stirrer, thermometer, condenser and addition funnel was added 0.5 moles of the appropriate ketone. The reaction flask was cooled by a dry ice-isopropanol bath and with rapid stirring 0.5 mole of the appropriate primary-alkylhydrazine was added dropwise. After the addition was complete the dry ice bath was removed and the reaction allowed to warm to room temperature. The reaction mixture was heated to reflux for 30 minutes and allowed to cool. The mixture was poured into 200 ml of water and extracted with pentane. The pentane extract was dried over anhydrous sodium sulfate, filtered and the pentane evaporated under reduced pressure on a flash evaporator. The residue was weighed, an infrared spectrum run on the material and the % yield of the alkylhydrazone determined. The infrared spectra of the alkylhydrazones were in agreement with their structures in all cases. The results are tabulated in Table I.

2. General Procedure B for the Preparation of Primary-alkylhydrazones

To a 250 ml 3 neck round bottom flask equipped with a magnetic stirrer, thermometer and Dean Stark trap containing a reflux condenser was added 0.1 mole of the appropriate n-alkylhydrazine, 0.1 mole of the appropriate ketone and 40 mls of benzene. The reaction mixture was heated to reflux and the water azeotroped with the benzene and collected in the Dean Stark trap. The reaction was refluxed until no more water formed. The reaction mixture was cooled to room temperature and the benzene evaporated under reduced pressure on a flash evaporator. The infrared spectra of the products were in agreement with the structure of an alkylhydrazone. The results are tabulated in Table I.

appearance of the primary-alkylhydrazone by gas chromatography. After the oxidation was approximately 50% complete, the reaction temperature was lowered to 25°–30° C and the oxidation completed.

Upon completion of the oxidation the temperature was lowered to 0° C by circulating ice water through the jacket. With rapid stirring 5% sodium sulfite solution was added in 50 ml increments to the hexane solution of the α-hydroperoxy azo compound while holding the reaction temperature at 5°–15° C. The reaction was monitored by gas chromatography where possible and by the exotherm generated during the reduction. When Table I

| | | Preparation of Primary-Alkylhydrazones | | | |
|---|---|---|---|---|---|
| Example | Primary-alkylhydrazine | Ketone | Method of Preparation | Product | % Yield |
| 1 | methylhydrazine | cyclohexanone | A | cyclohexanone methylhydrazone | 95 |
| 2 | methylhydrazine | methyl isobutyl ketone | A | methyl isobutyl ketone methylhydrazone | 31 |
| 3 | methylhydrazine | 2-heptanone | A | 2-heptanone methylhydrazone | 95 |
| 4 | methylhydrazine | methyl neopentyl ketone | A | methyl neopentyl ketone methylhydrazone | 85 |
| 5 | methylhydrazine | ethyl butyl ketone | A | 3-heptanone methylhydrazone | 88 |
| 6 | 2-hydroxyethylhydrazine | methyl isobutyl ketone | A | methyl isobutyl ketone 2-hydroxyethylhydrazone | 63 |
| 7 | 2-hydroxyethylhydrazine | cyclohexanone | A | cyclohexanone 2-hydroxyethylhydrazone | 49 |
| 8 | benzylhydrazine | acetone | A | acetone benzylhydrazone | 81 |
| 9 | benzylhydrazine | methyl ethyl ketone | A | methyl ethyl ketone benzylhydrazone | 100 |
| 10 | n-butylhydrazine | acetone | A | acetone n-butylhydrazone | 55 |
| 11 | n-butylhydrazine | methyl ethyl ketone | A | methyl ethyl ketone n-butylhydrazone | 42 |
| 12 | n-propylhydrazine | methyl ethyl ketone | A | methyl ethyl ketone n-propylhydrazone | 70 |
| 13 | n-propylhydrazine | acetone | A | acetone n-propylhydrazone | 83 |
| 14 | n-octylhydrazine | acetone | A | acetone n-octylhydrazone | 87 |
| 15 | n-octylhydrazine | methyl ethyl ketone | B | methyl ethyl ketone n-octylhydrazone | 95 |
| 16 | n-dodecylhydrazine | acetone | B | acetone n-dodecylhydrazone | 95 |
| 17 | n-dodecylhydrazine | methyl ethyl ketone | B | methyl ethyl ketone n-dodecylhydrazone | 94 |

General Procedure for the Oxidation of Primary-alkylhydrazones to the Corresponding α-Hydroperoxyazoalkanes and Subsequent Reduction to the Hydroxyazos Into a jacketed 250 ml reactor equipped with a mechanical stirrer, thermometer, condenser, oxygen inlet tube and gas exit tube was added the prescribed amount of the primary-alkylhydrazone and about 50 ml of hexane. The solution was warmed to 45° C and with rapid stirring oxygen was slowly bubbled into the solution. The reaction was monitored by following the disthe reduction was complete, the hexane solution was washed with saturated sodium bicarbonate solution, dried over anhydrous sodium sulfate, filtered, and the hexane evaporated on a flash evaporator at 0°–10° C. The residue was weighed, an infrared spectrum run on the product, and the % yield of the hydroxyazo determined. The infrared spectra of the hydroxyazos were in agreement with their structures in all cases. The results are tabulated in Table II.

Table II

| | Preparation of Primary-alkyl-α-hydroxyazoalkanes | | |
|---|---|---|---|
| Example | Starting Alkylhydrazone | Product | % Yield |
| 1 | cyclohexanone methylhydrazone | 1-methylazo-1-hydroxycyclohexane | 42 |
| 2 | methyl isobutyl ketone methylhydrazone | 2-methylazo-2-hydroxy-4-methylpentane | 56 |
| 3 | 2-heptanone methylhydrazone | 2-methylazo-2-hydroxyheptane | 83 |
| 4 | methyl neopentyl ketone methylhydrazone | 2-methylazo-2-hydroxy-4,4-dimethylpentane | 68 |
| 5 | 3-heptanone methylhydrazone | 3-methylazo-3-hydroxyheptane | 67 |
| 6 | methyl isobutyl ketone 2-hydroxyethylhydrazone | 2-(2-hydroxyethylazo)-2-hydroxy-4-methylpentane | 52 |
| 7 | cyclohexanone 2-hydroxyethylhydrazone | 1-(2-hydroxyethylazo)-1-hydroxycyclohexane | 38 |
| 8 | acetone benzylhydrazone | 2-benzylazo-2-hydroxypropane | 91 |
| 9 | methyl ethyl ketone benzylhydrazone | 2-benzylazo-2-hydroxybutane | 91 |
| 10 | acetone n-butylhydrazone | 2-n-butylazo-2-hydroxypropane | 45 |
| 11 | methyl ethyl ketone n-butylhydrazone | 2-n-butylazo-2-hydroxybutane | 86 |
| 12 | methyl ethyl ketone n-propylhydrazone | 2-n-propylazo-2-hydroxybutane | 37 |
| 13 | acetone n-propylhydrazone | 2-n-propylazo-2-hydroxypropane | 21 |
| 14 | acetone n-octylhydrazone | 2-n-octylazo-2-hydroxypropane | 98 |
| 15 | methyl ethyl ketone n-octylhydrazone | 2-n-octylazo-2-hydroxybutane | 99 |
| 16 | acetone n-dodecylhydrazone | 2-n-dodecylazo-2-hydroxypropane | 99 |
| 17 | methyl ethyl ketone n-dodecylhydrazone | 2-n-dodecylazo-2-hydroxybutane | 82 |

Evaluation of the Primary-alkyl-α-hydroxyazoalkanes as Polyester Foaming Agents The primary-alkyl-α-hydroxyazoalkanes were evaluated as foaming agents for unsaturated polyester resins using the following procedure. The results are tabulated in Table III.

To 100 grams of the unsaturated polyester resin (preparation described hereinbelow) were mixed 0.2 gram Lupersol DDM (Lucidol's methyl ethyl ketone peroxide formulation) or 1.0 gram t-butyl peroxybenzoate and the desired number of grams of the α-hydroxyazo (column labeled Parts Azo in Table III) using an electric stirrer. Finally the appropriate number of grams of an activator (if required) (columns labeled Activator and Parts Activator) was mixed into the formulation. The mixture was poured into a waxed cup at ambient temperature (75° F) and allowed to foam and cure. The foaming and curing were complete in less than 30 minutes. After the foams had cooled to room temperature the foam density was determined (column labeled Foam Density).

Note: The activator acetyl sec-hexyl-sulfonyl peroxide is designated as $AH_6SP$ in Tables III and IV. This was added as a 50% solution in dimethyl phthalate. The curing agent t-butyl peroxybenzoate is designated as tBPB in Tables III and IV.

of this unsaturated polyester were diluted with 3 parts of monomeric styrene to obtain a homogeneous blend having a viscosity of 21 to 35 poise and a specific gravity of 1.14 (the specific gravity of blend after curing in the absence of a foaming agent was 1.25—obtained by mixing 100 g of said blend with 1 g methyl ethyl ketone peroxide, then mixing therewith 0.2 g of a 6% solution of Co naphthenate with a gel time of 5.5 minutes, a cure time of 12 minutes and a peak exotherm of 330° F.). The above-described blend was used for the evaluations set forth in Tables III and IV.

Several α-hydroxyazo compounds derived from aldehydes were prepared and used to determine their capacity to foam polyester resins; the results are found in Table IV. Compare the results in Table III of Examples 1 to 6 and 8 to 17 (all of which are hydroxyazos derived from ketones) with the results in Table IV (hydroxyazos derived from aldehydes). The compounds in Table IV produced no foamed polymer in the absence of an activator. Moreover, the densities of the foams obtained from the hydroxyazos derived from ketones (Table III) were lower than the density of the foam obtained from the hydroxyazo derived from an aldehyde (Table IV). Examples 14 to 17 all gave high density foams without an activator. When a sulfonyl peroxide was used as the activator, a lower density was obtained.

Table III

| | Foaming of Polyester Resins with Primary-alkyl-α-hydroxyazoalkanes | | | | | |
|---|---|---|---|---|---|---|
| Example | Primary-alkyl-α-hydroxyazoalkane | Parts Azo | Curing Agent | Activator | Parts Activator | Foam Density (grams/c.c.) |
| 1 | 1-methylazo-1-hydroxycyclohexane | 2 | DDM | NONE | — | 0.839 |
| 2 | 2-methylazo-2-hydroxy-4-methylpentane | 2 | DDM | NONE | — | 0.317 |
| 3 | 2-methylazo-2-hydroxyheptane | 2 | DDM | NONE | — | 0.479 |
| 4 | 2-methylazo-2-hydroxy-4,4-dimethylpentane | 2 | DDM | NONE | — | 0.828 |
| 5 | 3-methylazo-3-hydroxyheptane | 2 | DDM | NONE | — | 0.312 |
| 6 | 2-(2-hydroxyethylazo)-2-hydroxy-4-methylpentane | 2 | t-BPB | NONE | — | 0.543 |
| 8 | 2-benzylazo-2-hydroxypropane | 2 | t-BPB | NONE | — | 0.484 |
| 9 | 2-benzylazo-2-hydroxybutane | 2 | t-BPB | NONE | — | 0.654 |
| 10 | 2-n-butylazo-2-hydroxypropane | 2 | t-BPB | NONE | — | 0.931 |
| 11 | 2-n-butylazo-2-hydroxybutane | 2 | t-BPB | NONE | — | 0.495 |
| 12 | 2-n-propylazo-2-hydroxybutane | 2 | t-BPB | NONE | — | 0.387 |
| 13 | 2-n-propylazo-2-hydroxypropane | 2 | t-BPB | NONE | — | 0.84 |
| 14 | 2-n-octylazo-2-hydroxypropane | 2 | t-BPB | $AH_6SP$ | 2 | 0.44 |
| 15 | 2-n-octylazo-2-hydroxybutane | 2 | t-BPB | $AH_6SP$ | 2 | 0.46 |
| 16 | 2-n-dodecylazo-2-hydroxypropane | 2 | t-BPB | $AH_6SP$ | 2 | 0.42 |
| 17 | 2-n-dodecylazo-2-hydroxybutane | 2 | t-BPB | $AH_6SP$ | 2 | 0.47 |

Table IV

| | Foaming of Polyester Resins with Prior Art Type Primary-alkyl-α-hydroxyazoalkanes | | | | |
|---|---|---|---|---|---|
| Primary-alkyl-α-hydroxyazoalkane | Parts Azo | Curing Agent | Activator | Parts Activator | Foam Density (grams/c.c.) |
| 1-methylazo-1-hydroxyheptane | 2 | DDM | NONE | — | NO FOAM |
| | 2 | DDM | $AH_6SP$ | 4 | 0.806 |
| 1-methylazo-1-hydroxy-2-methylpentane | 2 | DDM | NONE | — | NO FOAM |
| | 2 | DDM | $AH_6SP$ | 4 | 0.489 |
| 1-methylazo-1-hydroxypentane | 2 | t-BPB | NONE | — | NO FOAM |
| | 2 | t-BPB | $AH_6SP$ | 4 | 0.635 |
| 1-n-dodecylazo-1-hydroxy-2-methylpropane | 2 | t-BPB | $AH_6SP$ | 2 | 0.50 |

Preparation of an Unsaturated Polyester-Styrene Resin

An unsaturated polyester resin was prepared by reacting maleic anhydride (1.0 mole), phthalic anhydride (1.0 mole), and propylene glycol (2.2 moles) until an acid number of 45–50 was obtained. To this was added hydroquinone at a 0.013% concentration. Seven parts

What is claimed is:

1. Primary aliphatic-α-hydroxyazoalkane having the formula:

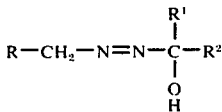

wherein
R is hydrogen, alkyl of 1 to 11 carbons, cycloalkyl of 3 to 12 carbons, bicycloalkyl of 3 to 12 carbons, tricycloalkyl of 3 to 12 carbons, aralkyl of 7 to 12 carbons, aryl of 6 to 14 carbons, alkaryl of 7 to 12 carbons;
$R^1$ is the same as R except $R^1$ is not hydrogen;
$R^2$ is the same as R except $R^2$ is neither hydrogen, aryl, nor alkaryl;
$R^1$ and $R^2$ taken together form an alkylene of 3 to 11 carbons.

2. The compound of claim 1 wherein R, $R^1$ and $R^2$ are the same or different alkyls of 1 to 11 carbons.

3. A compound according to claim 2 wherein said alkyl radicals contain 1 to 6 carbon atoms.

4. A compound according to claim 2 which is 2-methylazo-2-hydroxy-4-methylpentane.

5. A compound according to claim 2 which is 2-methylazo-2-hydroxyheptane.

6. A compound according to claim 2 which is 3-methylazo-3-hydroxyheptane.

7. A compound according to claim 2 which is 2-(2-hydroxyethylazo)-2-hydroxy-4-methylpentane.

8. A compound according to claim 2 which is 2-n-butylazo-2-hydroxybutane.

9. A compound according to claim 2 which is 2-n-propylazo-2-hydroxybutane.

10. The compound of claim 1 wherein R is aralkyl of 7 to 9 carbons.

11. A compound according to claim 10 which is 2-benzylazo-2-hydroxypropane.

12. A compound according to claim 10 which is 2-benzylazo-2-hydroxybutane.

* * * * *